(12) United States Patent
Gray et al.

(10) Patent No.: US 9,018,415 B2
(45) Date of Patent: Apr. 28, 2015

(54) PROCESS AND SYSTEM FOR THE SEPARATION AND DRYING OF CARBOXYLIC ACID CRYSTALS

(75) Inventors: Julian Stuart Gray, London (GB); Michael William Winter, London (GB); Andrea Gnagnetti, Milan (IT)

(73) Assignee: Davy Process Technology Limited, London (GB)

( * ) Notice: Subject to any disclaimer, the term of this patent is extended or adjusted under 35 U.S.C. 154(b) by 333 days.

(21) Appl. No.: 13/698,732

(22) PCT Filed: May 18, 2011

(86) PCT No.: PCT/GB2011/050944
§ 371 (c)(1),
(2), (4) Date: May 28, 2013

(87) PCT Pub. No.: WO2011/144935
PCT Pub. Date: Nov. 24, 2011

(65) Prior Publication Data
US 2013/0245317 A1    Sep. 19, 2013

(30) Foreign Application Priority Data

May 20, 2010    (GB) .................................. 1008412.7

(51) Int. Cl.
*C07C 51/47*    (2006.01)
*C07C 51/43*    (2006.01)

(52) U.S. Cl.
CPC ................. *C07C 51/47* (2013.01); *C07C 51/43* (2013.01)

(58) Field of Classification Search
None
See application file for complete search history.

(56) References Cited

U.S. PATENT DOCUMENTS

| 5,200,557 A | 4/1993 | Gee et al. |
| 2002/0003117 A1 | 1/2002 | Ohkoshi et al. |

FOREIGN PATENT DOCUMENTS

| CN | 1554637 | 12/2004 |
| CN | 101538199 A | 9/2009 |
| EP | 1671938 A1 | 6/2006 |
| WO | 9519335 A1 | 7/1995 |
| WO | 02053259 A2 | 7/2002 |
| WO | 2007145134 A1 | 12/2007 |
| WO | 2009024872 A2 | 2/2009 |

OTHER PUBLICATIONS

International Search Report and Written Opinion for PCT/GB2011/050944, dated Jul. 21, 2011, 13 pages.

*Primary Examiner* — Yevegeny Valenrod
(74) *Attorney, Agent, or Firm* — Armstrong Teasdale LLP

(57) ABSTRACT

In a process for the separation and drying of crude carboxylic acid crystals from a slurry in a solvent, the slurry is supplied to a filter operating at pressure and at a temperature above the atmospheric boiling point of the solvent. A cake of separated crystals is removed from the filter and passed to a thermal dryer. In a system for the separation and drying of crude carboxylic acid from a slurry in a solvent, a pressure filter device has a slurry inlet and an outlet for a cake of carboxylic acid crystals. The system also has a thermal dryer and means for transporting the cake of carboxylic acid crystals from the pressure filter device to the dryer. The pressure filter device is configured to operate at a pressure and temperature above the atmospheric boiling point of the solvent.

17 Claims, 2 Drawing Sheets

PROCESS AND SYSTEM FOR THE SEPARATION AND DRYING OF CARBOXYLIC ACID CRYSTALS

The present invention relates to a process for the separation and drying of crude carboxylic acid crystals, preferably crude aromatic carboxylic acid crystals, from a solvent and a system for said separation and drying. More particularly, it relates to the separation of crude terephthalic acid crystals or isophthalic acid crystals from acetic acid and a system for said separation and drying.

Typically crude terephthalic acid is produced by the oxidation of p-xylene. The oxidation is conducted using acetic acid as solvent in the presence of a catalyst. The solution is then cooled in a stepwise manner to crystallise the terephthalic acid. The terephthalic acid must then be removed from the acetic acid solvent and this is commonly carried out using a rotary vacuum filter, followed by a drying step to remove residual moisture.

A typical flow sheet for the prior art arrangement for the separation of the terephthalic acid is illustrated schematically in FIG. 1. Typically the crude terephthalic acid is fed as a slurry in line 1 in acetic acid to a rotary vacuum filter 2. An example of a rotary vacuum filter is described in US2002/0003117. Gas is added in line 20 and the filtrate and gas is removed in line 19.

In order for the separation process to take place under vacuum conditions, the feed to the rotary vacuum filter has to be cooled sufficiently, generally to about 90° C., so that the filtrate stream is below its boiling point at the vacuum pressure at which the filter operates. This is important since if the filtrate were to boil then further crystallisation would take place within the filter cloth of the rotary vacuum filter. This will lead to rapid cloth binding which requires the shut-down and cleaning of the rotary vacuum filter.

However, whilst operating the process at the lower temperature addresses the problems of crystallisation on the filter cloth, it means that the wet cake exiting the filter is at low temperature which causes problems in the downstream drying stage of the process.

Once settled as a cake on the filter, the terephthalic acid is washed with a clean acetic acid based solvent before being discharged in line 3 to a thermal dryer 4 where the acetic acid moisture is evaporated by heating. The direction of flow of the terephthalic acid cake is shown in FIG. 1 by arrow T.

As the cold wet cake enters the dryer 4 it contacts the acetic acid vapours that are discharged from the dryer since the vapour exits dryer 4 in countercurrent to the input of the cake. As the gaseous stream contacts the cold wet cake of terephthalic acid the acetic acid vapours may condense. This is disadvantageous since it will increase the moisture content of the cake which will increase the rate of fouling that occurs within the dryer and particularly within the cake inlet section thereof. When the dryer becomes fouled, the process has to be shut down while the equipment is cleaned. Cleaning requires washing with an alkali such as caustic soda which may increase the risk of corrosion. An increased rate of fouling will increase the frequency at which shut-down has to occur which, in turn, increases costs and reduces efficiency. Further, the fouling and cleaning requirements may lead to product quality issues.

In order to ensure that the amount of condensation that occurs in the cake inlet section of the dryer is minimised, a sweep gas is used to reduce the dewpoint of the vapour stream and to sweep the acetic acid vapours out of the dryer 4. Whilst this minimises the fouling problem, the amount of sweep gas required to maintain the vapour stream above its dewpoint has to be large. It is therefore not economical to operate a once through sweep gas flow.

As indicated by arrow G in FIG. 1, this sweep gas flows in countercurrent direction to the direction of flow of the terephthalic acid cake. The sweep gas, which is laden with the acetic acid vapours, exits from the dryer 4 at the same location that the wet cake is fed into the dryer.

The sweep gas generally originates from the offgas discharged from the oxidation reactor in which the p-xylene is oxidised to terephthalic acid. It will normally mainly comprise nitrogen, oxygen and carbon dioxide and is normally supplied from a portion of the reactor offgas which has been treated to remove carbon monoxide and other harmful substances. In one prior art process the offgas has to first be cooled and scrubbed to recover acetic acid and other valuable components before being treated to reduce the level of carbon monoxide and other organic compounds. The offgas stream is then fed to an expander to recover power before being discharged to atmosphere. Thus the more offgas which has to be diverted for use as the sweep gas, the less gas is passed through the expander and hence the less power that is recovered reducing the economics of the process.

It is therefore desirable to maximise the efficiency of the sweep gas process. This can only be achieved by a recirculation process. In order for the sweep gas to be recirculated, any particulates in the sweep gas discharged from the dryer 4 have to be removed, the acetic acid vapour has to be recovered and the resulting sweep gas has to be recompressed for feeding back to the dryer.

Whilst this arrangement addresses the fouling problems, it not only has a problem with loss of power recovered and the costs of operating the recirculation system, it is necessary to carefully control the amount of sweep gas used. Too much sweep gas results in a higher level of particulates becoming entrained in the sweep gas and this can result in blockages occurring in the sweep gas recirculation circuit. This is particularly a problem at the point where the sweep gas first discharges from the dryer. However, too little sweep gas results in condensation in the cake inlet section of the dryer which results in rapid fouling of the inlet section of the dryer such that the problems that the sweep gas was intended to address remain.

The discharged acetic acid and sweep gas leaving the dryer 4 is passed in line 5 to a scrubber 6. The gas is then scrubbed to remove particulates that have become entrained in the gas flow. However, an accumulation of particulates from the sweep gas can lead to fouling within the scrubber. This too will lead to a loss of production since the scrubber will periodically have to be shut down for cleaning.

The gas stream is scrubbed with cold solvent to condense the acetic acid vapours which need to be recovered. The scrubber includes a recirculation line 7. The recirculation stream is pumped by scrubber recirculation pump 8 and is then cooled in cooler 9 before being returned in lines 10 and 11 to the scrubber 6. A solvent purge is removed in line 21. The remaining sweep gas is removed from the scrubber 6 in line 12. Having been cooled in the scrubber the gas will have a temperature of about 40° C. It therefore has to be reheated in heater 13 to obtain a margin about the stream's dewpoint before being passed in line 14 to a blower 15 for return in line 16 to the dryer 4. A gas purge will be taken in line 17 and make-up gas can be added in line 18.

Since the dryer 4 operates at approximately atmospheric pressure the pressure profile around the sweep gas recirculation loop includes sections under partial vacuum pressure. There is therefore a potential for air to be sucked into the dryer 4 and if the oxygen level is not controlled, a flammable atmosphere can be formed which has the possibility of explosion occurring in the dryer due to the presence of acetic acid and terephthalic acid powder.

Once it is dry, the crude terephthalic acid is discharged from the dryer 4 in line 19 for further treatment.

Thus whilst the conventional process enables the crude terephthalic acid cake to be separated from the slurry from the reactor and dried, it is costly in terms of capital and operating costs due to the sweep gas requirements.

An alternative arrangement is described in CN101538199. Here it is suggested that the terephthalic acid should be dried under a micro-negative pressure. The method for drying the terephthalic acid under the micro-negative pressure controls the operation pressure in a dryer body to be between 0 millimeter $H_2O$ and −500 millimeter $H_2O$ so as to ensure that the dryer works in a micro-negative pressure environment. It is suggested that this offers an improvement on the surrounding working environment condition of the dryer, the reduction of the acid consumption and the prolongation of the service life of sealing components of the dryer. However, many of the problems of the conventional system including high capital and operating costs are still present.

Whilst the above problems have been discussed in connection with the separation of terephthalic acid, some or all of them occur with the separation of other crystalline carboxylic acids from the solvent in which the reaction to form them is carried out.

Alternative processes have been suggested. For example, U.S. Pat. No. 5,200,557 discloses a process in which multiple stage displacement washing with water is used to remove acetic acid from the slurry of crude terephthalic acid. Nitrogen is used to blow the liquid from the cake within the filter. Drying within the filter will generally only dry to about 10% moisture.

A similar process is described in CN1554637. In this process, the slurry is sent to a pressure filter. The dried cake is then treated to a washing and drying cycle within the filter.

Whilst these processes may provide some solutions, they leave a cake which has a relatively high moisture content, that is to say one with a moisture content of about 10%. A cake with a moisture content in this region presents various problems as it is difficult to handle and transport and cannot be stored in, for example, a silo.

It is therefore desirable to provide a process and system which allows for the successful separation of crude carboxylic acid crystals from the solvent in which the reaction to form the carboxylic acid is carried out. It is therefore desirable that the process and system allow for the efficient drying thereof. Further it is desirable that the process and system should overcome the problems associated with fouling of the dryer inlet noted with prior art arrangements, and preferably also reduces capital and operating costs. According to the present invention there is provided a process for the separation and drying of crude carboxylic acid crystals from a slurry in a solvent comprising the steps of:

supplying the slurry comprising crystals of carboxylic acid to a filter operating at pressure and at a temperature above the atmospheric boiling point of the solvent;

removing a cake of separated crystals from the filter; and passing said cake to a thermal dryer.

According to a second aspect of the present invention there is provided a system for the separation and drying of crude carboxylic acid crystals from a slurry in a solvent comprising:

a pressure filter device comprising a slurry inlet and an outlet for a cake of carboxylic acid crystals;

a thermal dryer; and means for transporting the cake of carboxylic acid from the filter device to the thermal dryer;

wherein said pressure filter device is configured to operate at a pressure and temperature above the atmospheric boiling point of the solvent.

The process and system of the present invention are suitable for use with any crystalline carboxylic acid but are particularly suitable for the separation of crude aromatic carboxylic acids. In one arrangement, they are for the separation of terephthalic acid or isophthalic acid from a slurry in acetic acid.

Any suitable pressure filter may be used with a rotary pressure filter being particularly preferred.

Since a pressure filter is used, unlike the vacuum system where the slurry for filtration has to be cooled, the pressure filter operates at a temperature above the boiling point of the solvent. Thus where the process relates to the separation of terephthalic acid from acetic acid, the filter will be operated at a temperature above the boiling point of acetic acid at atmospheric pressure.

The temperature and pressure at which the filter is operated will depend on the crystals to be separated. In one arrangement, which is particularly suitable where the crystals are those of crude terephthalic acid, the temperature of the filter may be from 110° C. to about 160° C. and the pressure may be from 2 to 5 bara.

With the process and system of the present invention, the cake of crystals discharged from the filter is much hotter than that discharged with the vacuum filtration system of the prior art. Thus for the separation of terephthalic acid from the acetic acid solvent, the temperature will be about 125° C. or above. The increased temperature means that the acetic acid vapours leaving the dryer do not contact a cold cake but rather contact a hot cake and as such there will be no condensation of the acetic acid onto the cake thereby minimising the fouling in the dryer. This will not only reduce the requirements for shutdown for alkaline wash, it will importantly substantially reduce the amount of sweep gas required.

Generally, the moisture content of the cake leaving the dryer will be from about 5% to about 20%. It may be from about 8% to about 15% or from about 10% to about 12%.

In a most preferred arrangement the requirement for sweep gas is removed completely, however, generally some will still be required. Generally, the level is sufficiently low that it becomes economical to operate a one-pass system. This means that there is no longer a requirement for a sweep gas recirculation system. This offers substantial savings in capital and operating costs. In addition, since the recirculation system is removed, there will be fewer pumps and blowers in the overall process which will make the process easier to operate and more reliable.

In a preferred arrangement the sweep gas flow in the dryer will be less than about 45 $m^3$/tonne of crude carboxylic acid such as terephthalic acid crystals. In a more preferred arrangement the sweep gas flow in the dryer will be less than 25 $m^3$/tonne of crude carboxylic acid, such as terephthalic acid, crystals. This is equivalent to 2000 $m^3$/hr at 80000 kg/hr of carboxylic acid production rate. More preferably the sweep gas flow in the dryer will be less than about 5 $m^3$/tonne of crude carboxylic acid, such as terephthalic acid, crystals. This is equivalent to 400 $m^3$/hr at 80000 kg/hr.

A further benefit of the arrangement of the present invention is that the amount of offgas from the reactor which can be passed to the expander to generate power is maximised further increasing the economics of the system. In addition, the requirement to expend power to run the recirculating blower is eliminated.

Since the amount of sweep gas utilised is reduced substantially, the gas velocity in the dryer is reduced which results in less entrainment of fines into the gas. It may alternatively, or additionally, mean that a smaller diameter dryer can be used for a given throughput.

Any suitable thermal dryer may be used. Typically a rotary steam tube dryer will be used but other dryer types such as paddle dryers or fluidised bed dryers may be used.

The crystals removed from the filter are generally passed directly to the dryer.

There is generally a flow of inert gas from the rotary valve that is connected between the dryer discharge for the dry crystals and the conveying system transporting the dry crystals onwards. This valve allows gas leakage back into the dryer. In one arrangement, this gas leakage is sufficient to act as the sweep gas such that no additional sweep gas is required.

The temperature at which the dryer operates will depend on the carboxylic acid and the solvent. Generally it will operate at a temperature above the dewpoint of the vapour stream. For the process for the separation of the crude terephthalic acid from acetic acid, the dryer will preferably operate above approximately 113° C. Thus the temperature will generally be from about 110° C. to about 160° C.

The pressure at which the dryer operates will depend the type of dryer being used but it will generally be from about 0 bara to about 5 bara.

Whilst various factors influence the final results, in one arrangement, the process of the present invention may achieve dried crystals having a moisture content of about 2% or less. In a preferred arrangement it will be from about 0.1 to about 1.0% moisture. In one arrangement, the moisture content achieved will be from about 0.2% to about 0.5%. The product with this low moisture content can be readily stored, transported and handled.

The present invention will now be described, by way of example, with reference to the accompanying drawings.

It will be understood by those skilled in the art that the drawings are diagrammatic and that further items of equipment such as reflux drums, pumps, vacuum pumps, compressors, gas recycle compressors, temperature sensors, pressure sensors, pressure relief valves, control valves, flow controllers, level controllers, holding tanks, storage tanks, and the like may be required in a commercial plant. The provision of such ancillary items of equipment forms no part of the present invention and is in accordance with conventional chemical engineering practice.

Figure 1:
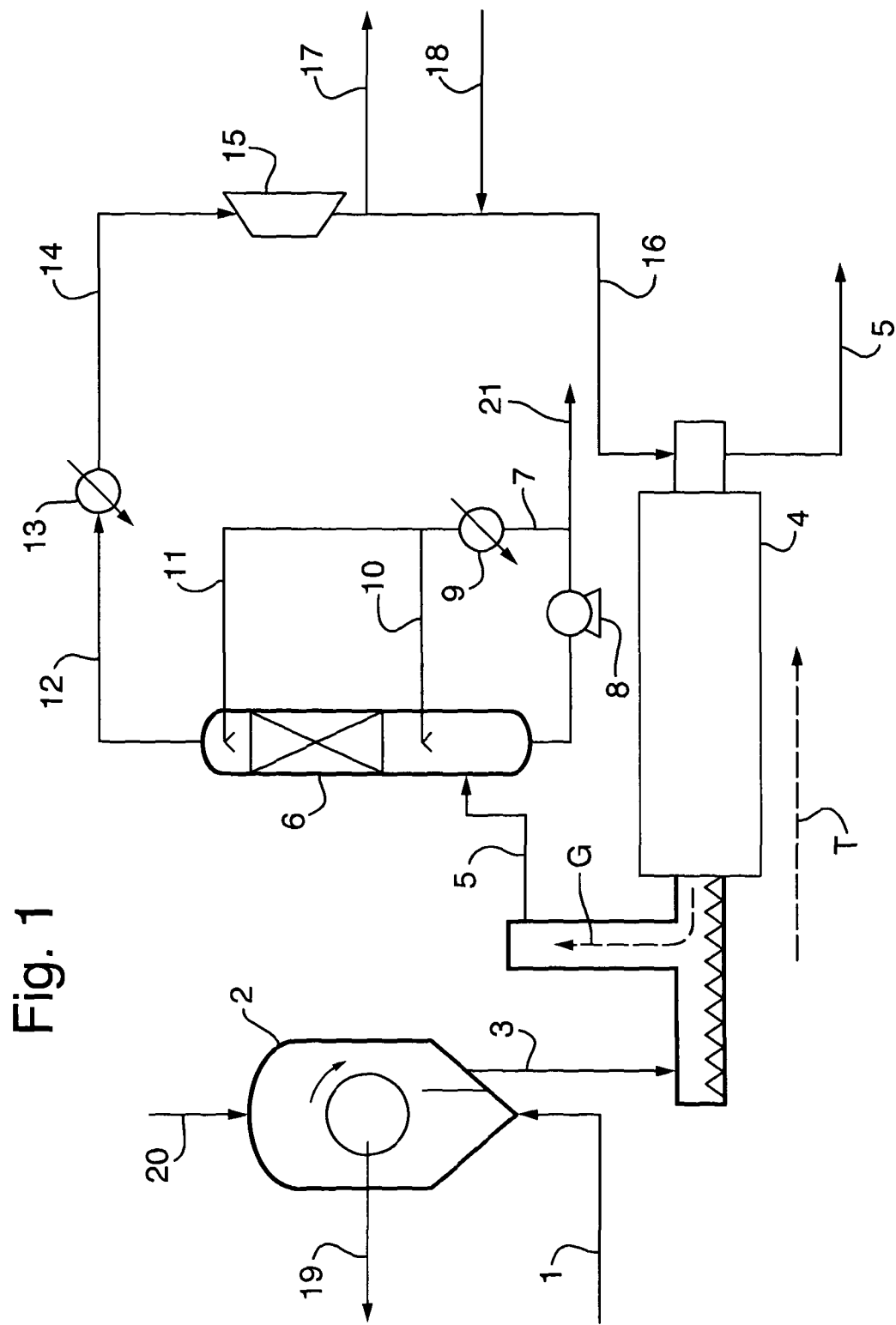
FIG. 1 is a schematic representation of the process and system under the prior art.
Figure 2:
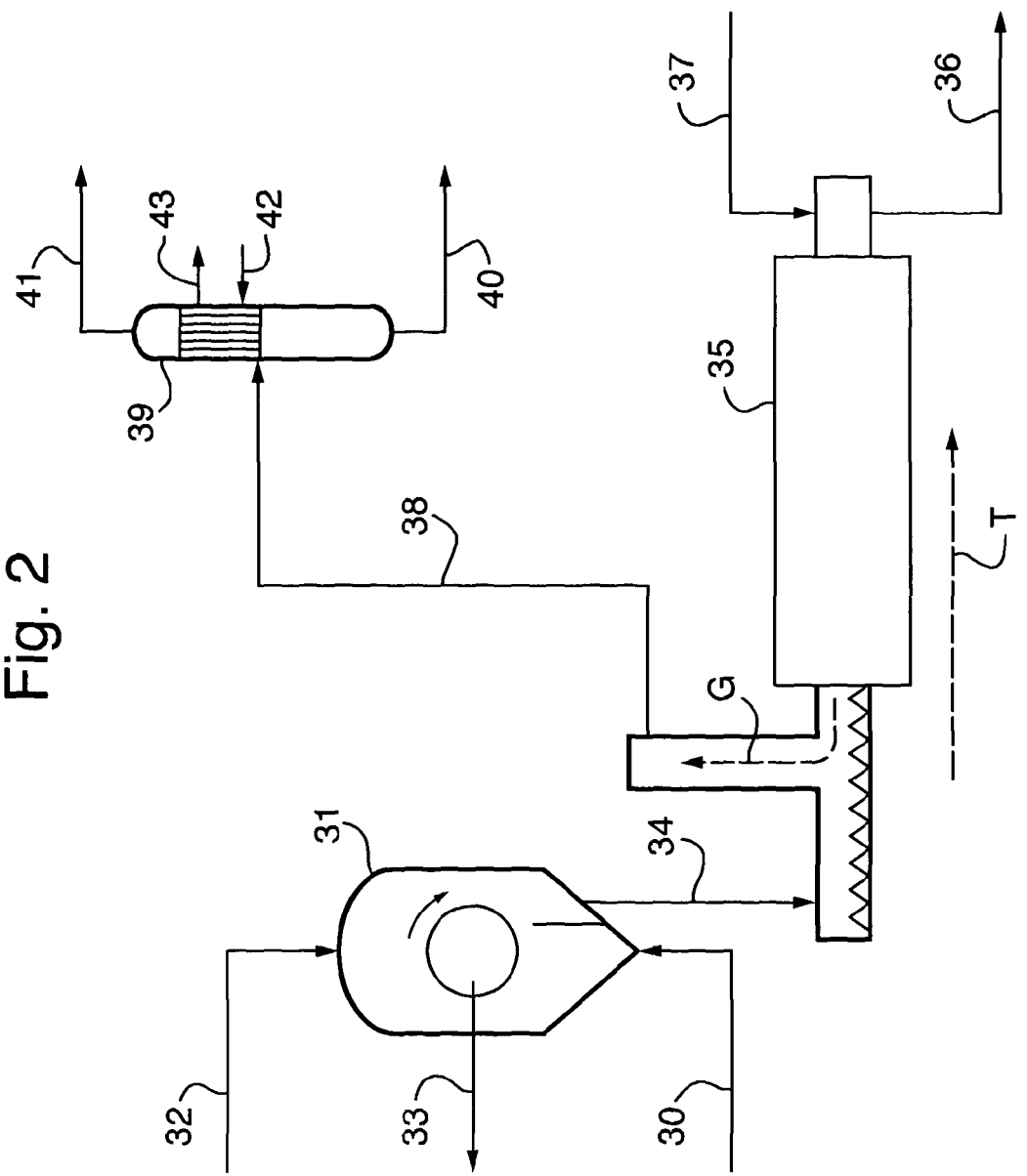
FIG. 2 is a schematic representation of the process and system according to the present invention.

By way of example, the process and system of the present invention will be described with reference to the separation of the terephthalic acid from acetic acid. As illustrated in FIG. 2, the slurry of terephthalic acid in acetic acid is passed in line 30 to a rotary pressure filter 31 where the crystals of terephthalic acid are separated from the acetic acid under pressure. Gas is introduced in line 32 and the filtrate and gas is removed in line 33. The cake of crystals of terephthalic acid are removed in line 34 and passed to the dryer 35. The direction of travel of the cake is illustrated by arrow T. The acetic acid vapour from the cake leaves the dryer in the direction of the arrow G. If a small amount of gas make up is required it will be added in line 37 and the dry terephthalic acid cake leaves in line 36 for onward treatment.

The acetic acid vapour and any sweep gas leaves the dryer in line 38 and is passed to condenser 39. The gas is cooled by contact with cooling tubes supplied with water flowing in line 42 and exiting in line 43. The condensed acetic acid is removed in line 40 and the small amount of sweep gas, if present, is removed in line 41.

It will therefore be seen that the equipment requirements are substantially reduced from those of the prior art arrangement illustrated in FIG. 2.

EXAMPLE 1 AND COMPARATIVE EXAMPLE 2

A process for the preparation of terephthalic acid is prepared and the crude acid as a slurry in the acetic acid is passed in Example 1 to a system according to the present invention using a rotary pressure filter and in Comparative Example 2 to a system according to prior art using a rotary vacuum filter. The examples are based upon a crude terephthalic acid production rate of 80,000 kg/h with a wet cake feed to the dryer with an acetic acid moisture content of 10%.

In Example 1, the wet cake temperature will be 115° C. With an assumed dewpoint margin of 5° C., sufficient nitrogen is added until the dewpoint of combined nitrogen/acetic acid vapour is 110° C. The resulting sweep gas flow rate will be 400 m$^3$/hr.

In Comparative Example 2, the wet cake temperature will be 90° C. With an assumed dewpoint margin of 5° C., sufficient nitrogen is added until the dewpoint of combined nitrogen/acetic acid vapour is 85° C. The resulting sweep gas flow rate will be 4000 m$^3$/hr.

It can therefore be seen that in this arrangement, the present invention gives a 90% reduction in the required sweep gas flow rate.

The invention claimed is:

1. A process for the separation and drying of crude carboxylic acid crystals from a slurry in a solvent, the process comprising the steps of:
supplying the slurry comprising crystals of carboxylic acid to a filter operating at pressure and at a temperature above the atmospheric boiling point of the solvent;
removing a cake of separated crystals from said filter; and
passing said cake to a thermal dryer, wherein a once pass sweep gas is provided to the dryer.

2. The process of claim 1 wherein the carboxylic acid is an aromatic carboxylic acid.

3. The process of claim 2 wherein the aromatic carboxylic acid is terephthalic acid or isophthalic acid and the solvent is acetic acid.

4. The process of claim 1 wherein the temperature of the filter is from 110° C. to about 160° C.

5. The process of claim 1 wherein the pressure of the filter is from 2 to 5 bara.

6. The process of claim 1 wherein the temperature at which the dryer operates is from about 110° C. to about 160° C.

7. The process of claim 1 wherein the pressure at which the dryer operates is from about 0 bara to about 5 bara.

8. The process of claim 1 wherein the flow of sweep gas in the dryer is less than about 45 m$^3$/tonne of crude terephthalic acid powder.

9. The process of claim 1 wherein the flow of sweep gas in the dryer is less than about 25 m$^3$/tonne of crude terephthalic acid powder.

10. The process of claim 1 wherein the flow of sweep gas in the dryer is less than about 5 m$^3$/tonne of crude terephthalic acid powder.

11. The process of claim 1 wherein sweep gas is not provided to the dryer.

12. The process of claim 1 wherein the moisture content of the carboxylic acid from the thermal dryer is about 2% or less.

13. The process of claim 1 wherein the moisture content of the carboxylic acid from the thermal dryer is about 1% less.

14. The process of claim 1 wherein the moisture content of the carboxylic acid from the thermal dryer is about 0.5% or less.

15. A system for the separation and drying of crude carboxylic acid from a slurry in a solvent, the system comprising:
   a pressure filter device comprising a slurry inlet and an outlet for a cake of carboxylic acid crystals;
   a thermal dryer configured to provide a once pass sweep gas; and
   means for transporting the cake of carboxylic acid crystals from the pressure filter device to the thermal dryer;
   wherein said pressure filter device is configured to operate at a pressure and temperature above the atmospheric boiling point of the solvent.

16. The system of claim 15 wherein the pressure filter device is a rotary pressure filter.

17. The system of claim 15 wherein the dryer is a rotary steam tube dryer.

\* \* \* \* \*